United States Patent
Walsh et al.

(10) Patent No.: US 12,256,940 B2
(45) Date of Patent: Mar. 25, 2025

(54) DEVICES, SYSTEMS, AND METHODS FOR OCCLUDING AN ANATOMICAL PASSAGE

(71) Applicant: BOSTON SCIENTIFIC SCIMED, INC., Maple Grove, MN (US)

(72) Inventors: Michael Walsh, Galway (IE); Gary Gilmartin, Foxford (IE); Louis McNern, Donegal (IE); Kevin McEvilly, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 17/740,343

(22) Filed: May 9, 2022

(65) Prior Publication Data
US 2022/0354503 A1 Nov. 10, 2022

Related U.S. Application Data

(60) Provisional application No. 63/186,329, filed on May 10, 2021.

(51) Int. Cl.
*A61B 17/12* (2006.01)
*A61B 17/00* (2006.01)

(52) U.S. Cl.
CPC .... *A61B 17/1215* (2013.01); *A61B 17/12099* (2013.01); *A61B 2017/00867* (2013.01); *A61B 2017/1205* (2013.01)

(58) Field of Classification Search
CPC .......... A61B 17/1215; A61B 17/12099; A61B 2017/00867; A61B 2017/1205; A61B 17/12168; A61B 17/12122; A61F 5/0079
See application file for complete search history.

(56) References Cited

U.S. PATENT DOCUMENTS

| | | | |
|---|---|---|---|
| 8,636,683 B2 | 1/2014 | Chin et al. | |
| 9,155,650 B2 | 10/2015 | Birk | |
| 9,622,897 B1* | 4/2017 | Stangenes | A61M 25/04 |
| 9,744,062 B2 | 8/2017 | O'Neill et al. | |
| 9,931,122 B2 | 4/2018 | Burnett et al. | |
| 9,943,299 B2 | 4/2018 | Khairkhahan et al. | |
| 10,219,931 B2 | 3/2019 | Fabian et al. | |
| 2004/0044361 A1 | 3/2004 | Frazier et al. | |

(Continued)

OTHER PUBLICATIONS

Trapezoid RX Biliary Brochure, Wireguided Retrieval Basket, pp. 1-4, 2016.

(Continued)

*Primary Examiner* — Sarah A Long
*Assistant Examiner* — Raihan R Khandker
(74) *Attorney, Agent, or Firm* — Seager, Tufte & Wickhem, LLP

(57) ABSTRACT

A device for occluding flow of materials is formed as a simple structure permitting a compact delivery configuration which may shift to an expanded deployment configuration. The device has at least one expandable portion formed of a plurality of elongated longitudinally extending frame elements. The frame elements may be spaced apart to define spaces therebetween, and a flexible occlusive material may be provided to block flow of material through such spaces. A flexible occlusive material may form one of two expandable portions of the device without the need for frame elements.

20 Claims, 8 Drawing Sheets

(56) References Cited

U.S. PATENT DOCUMENTS

| | | | |
|---|---|---|---|
| 2013/0030351 A1* | 1/2013 | Belhe | A61F 5/0079 |
| | | | 604/9 |
| 2014/0031849 A1 | 1/2014 | Gonzalez et al. | |
| 2014/0148842 A1* | 5/2014 | Khairkhahan | A61B 17/12122 |
| | | | 606/200 |
| 2015/0005810 A1* | 1/2015 | Center | A61B 17/0057 |
| | | | 606/200 |
| 2015/0209049 A1 | 7/2015 | Bernstein et al. | |
| 2017/0367710 A1 | 12/2017 | Yang | |
| 2019/0298559 A1* | 10/2019 | Gupta | A61B 17/29 |
| 2021/0228215 A1* | 7/2021 | Hill | A61B 17/12177 |
| 2022/0346997 A1* | 11/2022 | Fleury | A61F 5/0079 |

OTHER PUBLICATIONS

Trapezoid RX Wireguided Retrieval Basket, pp. 1-4, Mar. 11, 2021.
International Search Report and Written Opinion dated Aug. 12, 2022 for International Application No. PCT/US2022/028401.

* cited by examiner

DEVICES, SYSTEMS, AND METHODS FOR OCCLUDING AN ANATOMICAL PASSAGE

CROSS-REFERENCE TO RELATED APPLICATION

This application claims the benefit of priority of U.S. Provisional Application No. 63/186,329, filed May 10, 2021, the entire disclosure of which is hereby incorporated by reference herein for all purposes.

FIELD

The present disclosure relates generally to the field of devices, systems, and methods for occluding an anatomical passage. More particularly, the present disclosure relates to devices, systems, and methods for occluding the pylorus.

BACKGROUND

Various medical treatments involve occluding flow of materials through a body passage. For instance, treatment methods for various medical conditions, such as obesity, diabetes, or duodenal ulcers, involve restricting flow of materials through the duodenum or bypassing the duodenum. A duodenal exclusion device may be placed in the pyloric sphincter to inhibit or block (partially or fully) passage of materials (fluid, liquid, chyme, etc.) from the stomach through the pylorus and into the duodenum. It has become increasingly desirable to provide devices, systems, and methods which do not require open surgical procedures, but which instead use a transluminal or transcatheter approach, such as a fully endoscopic procedure (e.g., a natural orifice transluminal endoscopic surgery approach). Various challenges are presented by current occlusion devices such as during manufacture (e.g., ease of manufacture, cost, etc.), during delivery and deployment (e.g., size, profile, efficiency in delivery, etc.), and during use (e.g., efficacy, resistance to migration, ability to be removed, etc.).

With the above considerations in mind, a variety of advantageous medical outcomes may be realized by the devices, systems, and/or methods of the present disclosure.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, an occlusion device extends longitudinally between a first end and a second end, and includes a first expandable portion, a second expandable portion, and an intermediate region between the first expandable portion and the second expandable portion.

In one general aspect, an occlusion device formed in accordance with various principles of the present disclosure is configured to shift between a compact delivery configuration and an expanded deployed configuration.

In some embodiments, the occlusion device includes a plurality of elongated longitudinally extending frame elements forming a portion of at least one of the first expandable portion and the second expandable portion, the plurality of frame elements extending longitudinally when the occlusion device is in the compact delivery configuration and bending to a curved configuration when the occlusion device is in the expanded deployed configuration to define at least portion of the at least one of the first expandable portion and the second expandable portion. In some embodiments, an occlusive material is provided with respect to at least one of the first expandable portion and the second expandable portion to occlude flow of material through the at least one of the first expandable portion and the second expandable portion.

In some embodiments, the plurality of frame elements extend longitudinally in a direction extending between the first end of the occlusion device and the second end of the occlusion device leaving spaces between adjacent frame elements, and the occlusive material is provided with respect to the plurality of frame elements to occlude flow of material through the spaces between adjacent frame elements. In some embodiments, the occlusive material is in the form of a coating over the plurality of frame elements forming an occlusive barrier through the spaces between adjacent frame elements. In some embodiments, the frame elements form a frame over which the occlusive material is positioned to occlude flow of material through the spaces between adjacent frame elements. In some embodiments, the occlusion device further includes a scaffold structure over which the occlusive material is formed.

In some embodiments, the occlusive material covers a portion of the at least one of the first expandable portion and the second expandable portion adjacent the intermediate region of the occlusion device.

In some embodiments, the first expandable portion is configured to be seated in a stomach adjacent a pylorus; the second expandable portion is configured to be seated in a duodenum adjacent a pylorus; the intermediate region is configured to extend through the pylorus; and the occlusive material is selected to occlude flow of chyme therethrough.

In some embodiments, the intermediate region is defined by one or more of the frame elements. In some embodiments, a collar is disposed over the intermediate region to retain the one or more of the frame elements together to define the intermediate region.

In some embodiments, at least a portion of both the first expandable portion and the second expandable portion are formed from the plurality of frame elements. In some embodiments, one or more of the plurality of frame elements is formed from first and second frame elements coupled together along ends thereof. In some embodiments, the first and second frame elements forming one or more of the plurality of frame elements are coupled along the intermediate region of the occlusion device. In some embodiments, at least one of the plurality of frame elements extends along both the first expandable portion and the second expandable portion.

In some embodiments, the plurality of frame elements are formed from shape memory material and shift between a substantially straight configuration, when the occlusion device is in the delivery configuration, and a nonlinear configuration, when the occlusion device is in the deployed configuration, to define a portion of the at least one of the first expandable portion and the second expandable portion.

In some embodiments, the first expandable portion is defined by the occlusive material without frame elements, and the second expandable portion is formed of the frame elements.

Additionally or alternatively, in one general aspect, an occlusion device formed in accordance with various principles of the present disclosure is configured to occlude flow of material through a body passage.

In some embodiments, the first expandable portion is configured to shift between a compact delivery configuration and an expanded deployed configuration; and the second expandable portion is configured to shift between a compact delivery configuration and an expanded deployed configuration. In some embodiments, the occlusion device includes an intermediate region between the first expandable portion and the second expandable portion.

In some embodiments, at least three elongated frame elements extend longitudinally between the first end of the occlusion device and the second end of the occlusion device and define at least a portion of the first expandable portion and the second expandable portion. In some embodiments, the frame elements are formed from shape memory material and shift between a substantially straight delivery configuration when constrained by a delivery device and a nonlinear deployed configuration when unconstrained to define at least a portion of a contour of the first expandable portion and the second expandable portion.

In some embodiments, the plurality of frame elements are spaced apart leaving spaces therebetween. In some embodiments, the occlusion device further includes an occlusive material covering the spaces between frame elements at least along the first expandable portion of the occlusion device.

In accordance with various principles of the present disclosure, a system for occluding flow of material through a body passage includes a delivery device including a flexible tubular element with a delivery lumen defined therein, and an occlusion device configured to fit within the delivery lumen of the flexible tubular element in a compact delivery configuration and to expand into an expanded deployed configuration when deployed out of the delivery device. In some embodiments, the occlusion device includes a first expandable portion adjacent a first end of the occlusion device and a second expandable portion adjacent a second end of the occlusion device, and an intermediate region therebetween. In some embodiments, at least one of the first expandable portion and the second expandable portion is formed from a plurality of elongated frame elements extending in a direction between the first end of the occlusion device and the second end of the occlusion device, and spaced apart from one another to leave spaces between adjacent frame elements. In some embodiments, the frame elements are formed of shape memory material and are held in a substantially straight elongated configuration within the flexible tubular element of the delivery device when the occlusion device is in the compact delivery configuration, and shift to a nonlinear configuration to define a contour of at least one of the first expandable portion and the second expandable portion in an expanded deployed configuration of the occlusion device.

In some embodiments, the system further includes an occlusive material provided with respect to at least one of the first expandable portion and the second expandable portion to occlude flow of material through the at least one of the first expandable portion and the second expandable portion, the occlusive material being collapsible to a compact delivery configuration when the occlusion device is within the flexible tubular element of the delivery device.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
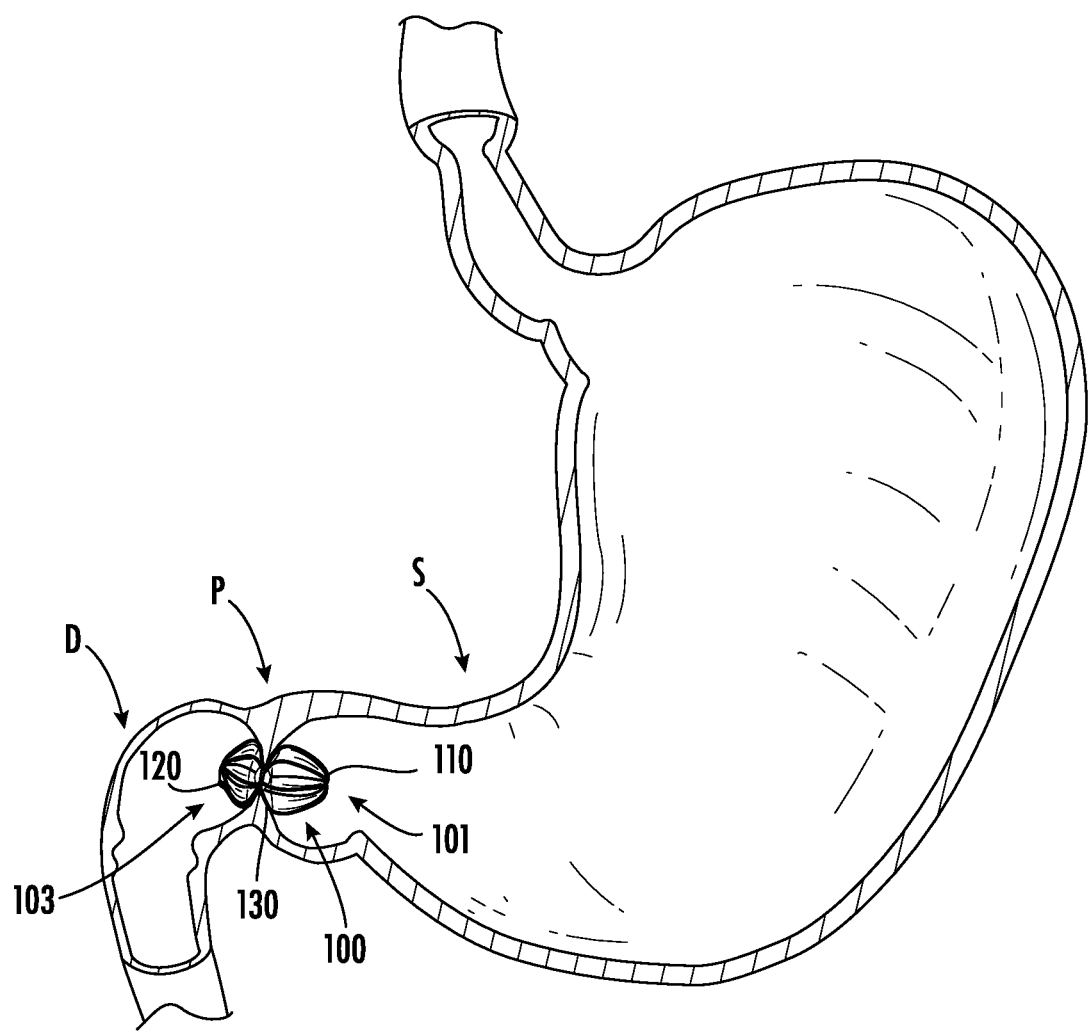
FIG. 1 illustrates a perspective view of an embodiment of an occlusion device formed in accordance with various aspects of the present disclosure and positioned in a schematic representation of a gastrointestinal environment.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point or central region, and a "central axis" means, with respect to an opening, a line that at least generally bisects a center point of the opening, extending longitudinally along the length of the opening when the opening comprises, for example, a tubular element, a channel, a cavity, or a bore.

In accordance with various principles of the present disclosure, a device and associated systems and methods are provided to reduce passage of material through an anatomical structure. The term anatomical structure may be used herein to reference any structure or section or region or area in the body such as a body passage, lumen, organ, vessel, cavity etc.. It will be appreciated that reference may be made specifically to a body passage and/or lumen for the sake of convenience, and such terms may be used interchangeably herein without intent to limit, the broad principles of the present disclosure being applicable to various other anatomical structures. In some embodiments, the device, system, and methods occlude (fully or substantially fully) passage of material through the body passage or lumen. For the sake of convenience, a device formed in accordance with various principles of the present disclosure may be referenced herein as an occlusion device without intent to limit. It will be appreciated that references to occlusion (and other conjugations and grammatical forms thereof) includes partial occlusion (partially restricting, such as reducing flow of materials) as well as full occlusion (fully restricting flow of materials). Moreover, it will be appreciated that terms such as prevent, restrict, inhibit, occlude, block, etc. (and conjugations and other grammatical forms thereof) may be used interchangeably herein without intent to limit unless otherwise indicated. Finally, it will be appreciated that reference may be made to the body passage at which the occlusion device is deployed or positioned and/or through or across which a portion of the occlusion device is deployed or is positioned or extends, and, more generally, to a deployment site, all such references and similar references being used interchangeably herein without intent to limit unless otherwise indicated.

Generally, an occlusion device formed in accordance with various principles of the present disclosure is configured to shift between a delivery configuration and a deployment configuration. In the delivery configuration, the occlusion device is generally compact to facilitate delivery to (or removal from) the deployment site, and may be collapsed or compressed or constrained or otherwise positioned and maintained in a compact configuration within a delivery device. The delivery device may include a tubular member, such as a catheter, sheath, shaft, tube, etc., in which the occlusion device is transported. The tubular member may be generally elongate and generally flexible such as to facilitate transluminal delivery of the occlusion device (in contrast with open surgery), even along tortuous pathways. In general, the smaller the diameter of the occlusion device, the more readily the device may be transported through a patient's body, such as through a tortuous pathway within (e.g., transluminally instead of through a surgical opening) the patient's body. More particularly, since the occlusion device typically is delivered within the delivery device (e.g., within a flexible tubular member), the smaller the profile of the occlusion device (e.g., the smaller the diameter and/or volume occupied by the occlusion device), the smaller (e.g., narrower) the delivery device that may be used, and the easier the maneuvering of the delivery device with the occlusion device therein to the deployment site. Once deployed, the occlusion device may be expanded to a deployment configuration to occlude a body passage.

If the body passage includes a passage between different anatomical structures, an occlusion device formed in accordance with various principles of the present disclosure may be considered to have a first portion configured to fit or to be seated within or against a first anatomical structure, a second portion configured to fit or to be seated within or against a second anatomical structure, and an intermediate region (alternately referenced herein as a saddle region without intent to limit) therebetween. The first portion and the second portion may be referenced herein as expandable portions, as such portions are generally expanded from a compact delivery configuration when deployed. In the expanded configurations, the first and second portions are configured to occlude flow of material, such as through a body passage generally narrower than the first and/or second portion when such portion is in an expanded configuration. The first portion and/or the second portion of the occlusion device may be seated against an inlet/outlet of the body passage, and/or against tissue (e.g., tissue walls) surrounding the body passage to occlude flow through such body passage. The intermediate region is configured to extend through or along the passage between the first and second anatomical structures, and preferably is sufficiently long to extend through a body passage without the first or second portions extending into the body passage as well. It will be appreciated that terms such as fit or seat or position or the like (and conjugations thereof) may be used interchangeably herein without intent to limit unless otherwise indicated. Furthermore, it will be appreciated that reference herein to seating within or against or with respect (such terms being used interchangeably herein without intent to limit) to a body passage includes, without limitation, seating with respect to the tissue wall surrounding the body passage and/or seating with respect to the inlet to the body passage through which flow of materials is to be occluded.

In some embodiments, the first portion and the second portion may be considered retention members which retain or hold the occlusion device in place with respect to the body passage to effect the desired occlusion of flow of materials through the body passage. For instance, in general, it is desirable for at least one portion of the occlusion device to remain seated with respect to a body passage (through which flow is to be occluded) after deployment of the occlusion device so that flow is occluded as desired. The first portion and the second portion of the occlusion device may be configured to hold each other in place with respect to the deployment site.

If flow of material to be occluded is generally more commonly in one direction than another opposite direction, then the first and second portions of the occlusion device may be considered upstream and downstream portions. The upstream portion, as referenced herein, is positioned along an end of the occlusion device with respect to the deployment site upstream of the typical direction of flow to be occluded. The downstream portion, as referenced herein, is positioned along the other end of the occlusion device, opposite the upstream end, and downstream of the typical direction of flow to be occluded. In some embodiments, an occlusion device formed in accordance with various principles of the present disclosure is shaped and configured so that at least the upstream portion of the occlusion device remains seated with respect to a body passage after deployment and is configured to occlude flow of materials through the body passage. The downstream portion of the occlusion device preferably is shaped and configured to be seated with respect to the deployment site at least so that the occlusion device does not shift with respect to the deployment site so that at least the upstream portion successfully occludes flow of material. In some embodiments, the downstream portion is also be configured to occlude flow of material.

Various existing occlusion devices are configured to shift between a compact delivery configuration and an expanded deployment configuration. Such occlusion devices have various levels of complexity of structure and/or the mechanism of shifting the device between the delivery and deployment configurations. An occlusion device formed in accordance with various principles of the present disclosure reduces complexities in structure as well as deployment into an expanded passage-occluding deployment configuration.

In some embodiments, at least a portion of an occlusion device formed in accordance with various principles of the present disclosure is formed with a plurality of elongated elements (such as strands, wires, filaments, etc.) arranged such as to form a frame. It will be appreciated that terms such as strands, wires, filaments, etc. may be used interchangeably herein without intent to limit, and the elements may be generally referenced herein as frame elements for the sake of convenience and without intent to limit. The frame elements may form one or both of the expandable portions of the occlusion device. In some embodiments, at least three frame elements extend longitudinally along an expandable portion of the occlusion device and are configured to be spaced apart from one another to form an expandable portion of the occlusion device when the occlusion device is in a deployed configuration with less material than used in prior occlusion devices.

In accordance with various principles of the present disclosure, the frame elements are configured to form or to contribute to forming an expanded configuration of the occlusion device in the deployment configuration from a relatively compact configuration facilitating delivery. The frame elements may be configured to shift from an elongated, generally straight or extended configuration, when the occlusion device is in a delivery configuration, to a curved or bent or contoured or nonlinear or otherwise not straight configuration in the expanded deployment configuration. The shapes of the frame elements together define at least a portion of (e.g., a contour of) at least one of the expandable portions of the occlusion device. The shape (e.g., curvature) of the frame elements upon deployment preferably is selected to form the desired contour of the associated expandable member to effect the desired occlusion of flow of materials. For instance, the shape of the frame elements may be selected to ensure secure seating of the associated expandable member with respect to a passage to be occluded by the occlusion device. In some embodiments, such as described in further detail below, an occlusive material is provided with respect to the frame elements such that the frame elements along with the occlusive material define the contour or shape of at least one of the expandable portions.

Each of the proximal portion and the distal portion of the occlusion device when in the deployment configuration is shaped and configured to be sufficiently large (e.g., have a sufficiently large diameter) as to not pass through the body passage across which the intermediate region is positioned so that the occlusion device is held in place against migration to prevent undesired passage of materials through the body passage as well as undesired migration of the occlusion device into other areas of the body. It will be appreciated that selection of materials, resiliencies, shapes, sizes, and configurations, among other properties as may be appreciated by those of ordinary skill in the art, of the frame elements also may contribute to the ability of the first and second portions to hold the occlusion device in place against migration. It is noted that such terms as inhibit, prevent, or resist (including conjugations and other grammatical forms thereof) with reference to holding the occlusion device against migration may be used interchangeably herein without intent to limit.

In some embodiments, the frame elements are pre-shaped into a configuration suitable for the expanded configuration of the occlusion device (e.g., to form or to contribute to forming the expanded first and second portions of the occlusion device) so that the frame elements form the desired configurations of the first and second portions of the occlusion device upon deployment without further manipulation of the frame elements. For instance, the frame elements may be held in a generally straight configuration (e.g., when positioned within a delivery device) to allow for the occlusion device to be in a compact configuration, but may shift on their own to a shape or configuration forming or contributing to forming one of the expandable portions of the occlusion device when in the deployed configuration. In other words, the frame elements may be curved or otherwise shaped in a nonlinear manner when in a neutral or rest configuration such that the frame elements naturally return to such configuration if released from a substantially straight deployment configuration. Advantageously, the frame elements may be formed from a shape memory material and/or heat-formable material (e.g., a nickel titanium alloy such as Nitinol, or a cobalt-chromium-nickel-molybdenum alloy such as Elgiloy), shaped into the desired contour for an associated expandable portion of the occlusion device. In some embodiments, the frame elements are configured to form at least a portion of the desired contour of at least one of the expandable portions of the occlusion device when in the deployed configuration so that no further adjustment of the occlusion device and/or the frame elements is necessary to achieve the desired occlusion of flow of materials. For instance, the expanded configuration of at least one of the frame elements may be shaped to follow the contour of the anatomical structure along which such at least one frame element is positioned so that the expandable portion may seat against such structure to effect the desired occlusion of flow of materials. A further element may be provided, such as described in further detail below, to contribute to occlusion of flow of materials through spaces between the frame elements. The frame elements may be pre-shaped to expand outwardly (e.g., from the intermediate region and/or along a longitudinal axis of the occlusion device) to form a sufficiently wide frame so as not to pass through the body passage through which the intermediate region is positioned. Externally applied forces may allow return of the expanded portions to collapsed or compact configurations (e.g., with reduced diameters, such as to facilitate transluminal delivery or removal), such as by straightening the frame elements, but such shifting should generally not occur from internal natural bodily forces thereon. In other words, shifting to a collapsed or compact configuration does not occur without intended external forces not normally occurring within the body.

In some embodiments, the frame elements extend generally longitudinally from a first end of the occlusion device to a second end of the occlusion device. In some embodiments, at least one of the frame elements is a continuous element extending from the first end of the occlusion device to a second end of the occlusion device. In the expanded configuration, if the same frame element extends from the first end of the occlusion device to the second end of the occlusion device, then such frame element generally shifts along a first portion thereof (adjacent the first end of the occlusion device) to form an expanded first portion of the occlusion device, and along a second portion thereof (adjacent the second end of the occlusion device) to form an expanded second portion of the occlusion device. For instance, a frame element extending along the occlusion device to form both expandable portions of the occlusion device may be S-shaped or otherwise shaped to form a portion of two adjacent expandable portions of an occlusion device formed in accordance with various principles of the present disclosure. Preferably, at least one frame element extends across both expandable portions of the occlusion device, such as to ensure the portions do not separate from each other.

In some embodiments, one or more of the frame elements may comprise two or more elements connected end to end (colinearly or overlapped) and extending from a first end of the occlusion device to a second end of the occlusion device. A frame element forming only one of the expandable portions of an occlusion device may be generally C-shaped or otherwise shaped to form a portion of an expandable portion of an occlusion device formed in accordance with various principles of the present disclosure. Use of different elements along a given frame element permits selection of properties suitable for the portion of the occlusion device formed by such element. For instance, if the occlusion device is subjected to greater forces on one side thereof (e.g., upstream of a dominant flow direction of materials to be occluded by the occlusion device), then the portion on such side (e.g., the upstream portion) may be formed of frame elements more resistant to returning to the elongated generally straightened configuration of the delivery configuration of the occlusion device to resist migration of the occlusion device. For instance, the frame elements along the first expandable portion of the occlusion device may have a different stiffness, resiliency, diameter, etc., and/or be formed of a different material, and/or have other properties than the frame elements along the second expandable portion of the occlusion device. Additionally or alternatively, a greater number of frame elements may extend along one of the expandable portions than the other of the expandable portions, with more than one frame element of such one expandable portion being coupled to a given frame element of the other expandable portion (formed of fewer frame elements). The connected ends of multiple elements forming a frame element may be coupled together in any desired manner providing a secure connection so that the elements remain together. For instance, the adjacent ends may be crimped and coupled together (or otherwise mechanically shaped and attached/linked), welded or crimped or glued or bonded or otherwise fused together (either with abutting or overlapping ends), or covered and held together with a separate coupling element (e.g., a coupling sleeve or a sealant, such as silicone). For the sake of convenience, and without intent to limit, reference is simply made to coupled. If a frame element is formed from one or more elements connected end to end, at least one connection between the connected elements may be along the intermediate region of the occlusion device.

The intermediate region of the occlusion device may distinguish the first expandable portion from the second expandable portion. For instance, frame elements extending through the intermediate region generally do not bend from their generally elongated and straight delivery configuration when the occlusion device is shifted into the deployment configuration. In some embodiments, the frame elements define the intermediate region such that the intermediate region does not define a lumen directing flow of materials therethrough. In other words, an occlusion device with at least a portion thereof formed from a plurality of frame elements may not include a generally tubular intermediate region with a lumen therethrough as in prior art occlusion devices. Materials may thus flow through spaces between adjacent frame elements extending through and defining the intermediate region. In some embodiments, a collar (e.g., band, ring, tube, cuff, strand of material, etc., reference being made herein to a collar for the sake of convenience and without intent to limit) may extend around the frame elements to maintain the frame elements together, and may define a generally narrowed intermediate region of the occlusion device. Such collar preferably is of limited longitudinal extent (to have minimal effect on the occlusion device) and need not define a lumen for passage of materials through the occlusion device. In other words, such collar may have a limited extent along the longitudinal axis of the occlusion device to hold frame elements with respect to one another but not to define a lumen through the occlusion device.

It will be appreciated that the use of a plurality of spaced apart elongate elements, such as longitudinally extending elongated elements, as disclosed herein permits formation of a simpler structure than that of prior art occlusion devices. For instance, less material may be used (such as compared with a woven or tubular structure), and a simpler manufacturing process may be used (such as compared with a woven or laser-cut tubular structure).

The use of less material than in previous occlusion devices may facilitate formation of an occlusion device with a more compact delivery configuration than prior occlusion devices, facilitating minimally invasive delivery, such as transluminal or transcatheter or transcatheter or endoscopic delivery (and generally avoiding more complex and/or invasive open surgery) and/or facilitating navigation through tortuous body passages. In accordance with various principles of the present disclosure, the use of relatively thin elongated frame elements which are spaced apart from one another allows the adjustable tubular device to be sized and configured more compactly than tubular structures of prior occlusion devices to facilitate delivery. For instance, elongated elements with diameters of as thin as approximately 0.006 in (0.015 cm) and up to approximately 0.008 in (0.020 cm), including increments of 0.0001 in (0.0025 mm) therebetween, may be used to form frame elements defining at least portions of an occlusion device in accordance with various principles of the present disclosure. In some embodiments, the frame elements may have diameters as little as 0.002 in (0.005 mm), though other modifications (e.g., different materials or increased number of elements) may be appropriate to achieve the desired overall properties of the expandable portion along which such frame elements extend.

In accordance with another aspect of the present disclosure, the use of less material than in previous occlusion devices may facilitate the formation of an occlusion device with an intermediate region narrower than those of prior occlusion devices. For instance, the intermediate region of an occlusion device formed in accordance with various principles of the present disclosure may be smaller (e.g., have a smaller diameter) or may be more compact than the intermediate region of prior occlusion devices such as tubular occlusion devices (e.g., woven or braided devices, or devices formed from initially solid-walled tubes). The intermediate region need not have a defined/pre-defined lumen therethrough, which may further facilitate manufacture and reduce other design complexities and/or allow for a smaller profile in a deployed configuration than achieved by other occlusion devices. For instance, in some embodiments, at least one of the first and second expandable portions is configured to occlude the flow of materials through a body passage through which the intermediate region extends so that the occlusive effect of the intermediate region is not critical to the functioning of the occlusion device. The intermediate region may in some embodiments consist essentially of simply and only one or more frame elements. In some embodiments, the intermediate region simply extends across the body portion to connect (e.g., hold together) the first expandable portion and the second expandable portion so that such expandable portions effectively occlude flow of materials as desired. A narrower (in diameter) intermediate region may be desirable if minimal interference with the function of the pylorus is desired. For instance, it may be desirable not to affect the function (e.g., natural movements) of the pylorus, and to rely on the configuration and properties of the expandable portions of the occlusion device to occlude flow of materials through the pylorus. In some instances, it may be desirable to reduce interaction of the occlusion device with the pylorus such as to reduce possible reactions of the pylorus to expel the occlusion device therefrom.

In accordance with various principles of the present disclosure, an occlusive material (a material occluding flow of other materials therethrough) may be provided to close or cover or fill gaps or spaces between spaced apart frame elements forming at least a portion of the occlusion device. The occlusive material may be in the form of a coating or covering over a plurality of frame elements, the occlusive material forming an occlusive barrier through the spaces between adjacent frame elements. The occlusive material may be selected to occlude materials specific to the deployment site (e.g., chyme in an embodiment in which the occlusion device is positioned across a pylorus). Examples of occlusive materials include biocompatible silicones, polytetrafluoroetheylene (PTFE), polyurethane (PU), polyolefin (such as polyethylene (PE) or polypropylene (PP)), etc. It will be appreciated that terms such as close, cover, fill, occlude, block, etc. (and various conjugations and grammatical forms thereof) may be used interchangeably herein without intent to limit unless otherwise noted. The occlusive material may be formed separately (such as in the form of a separate covering element) and applied or extended over at least a portion of the frame elements. As may be appreciated, the frame elements may be considered to form a frame on which the covering element may be disposed. Alternatively or additionally, occlusive material may be applied to at least a portion of the occlusion device, such as a portion of the frame elements, in a liquid form which solidifies to achieve the desired occlusive properties of the occlusive material. For instance, the occlusion device may be coated with or dipped into a liquid form of the occlusive material (e.g., a bath of occlusive material), or the occlusive material may be sprayed over the frame elements. In some embodiments, a net or mesh is provided as a thin flexible scaffold (sufficiently thin as to not impact the overall dimensions of the occlusion device when in a compact configuration) for application of an occlusive material thereto. The net or mesh may be formed of any suitable biocompatible material, such as synthetic surgical mesh, including, without limitation, polypropylene, polyester, or PTFE mesh. In some embodiments, additional frame elements thinner than the frame elements structurally contributing to anti-migration and desired seating of the occlusion device may be provided to support a covering member (yet thinner than generally desired or needed to hold the occlusion device in place with respect to the deployment site in a manner as described above). Preferably, in all or most such embodiments, the occlusive material is sufficiently flexible to allow the occlusion device to collapse into a compact configuration facilitating delivery to the deployment site as well as removal therefrom (if desired).

In accordance with various principles of the present disclosure, at least one portion of the occlusion device is covered with an occlusive material (such as described above) to block flow of material through the body passage to be occluded by the occlusion device. If flow of materials is generally more commonly in one direction than another opposite direction, then at least the upstream portion of the occlusion device (upstream of the more common direction of flow) is provided with an occlusive material in any desired manner (including but not limited to those described above) to prevent flow of materials therethrough and downstream of the body passage. In some embodiments, the downstream portion of the occlusion device is optionally covered as well. However, if the upstream portion is sufficiently securely seated against the inlet to the body passage to occlude flow therethrough, or otherwise configured or positioned to sufficiently occlude flow of materials through the body passage, then a covering over the downstream portion of the occlusion device may not be necessary.

In some embodiments, the occlusive material may inhibit tissue ingrowth to further facilitate removal of the occlusion device. In some embodiments, a removal device, such as a loop of material (e.g., a suture, wire, string, or other material), may be provided at a proximal end of the occlusion device to facilitate grasping and pulling of the occlusion device to withdraw the occlusion device, and may return the occlusion device to a compact configuration to facilitate removal. On the other hand, some level of tissue ingrowth may be desirable to contribute to holding the occlusion device in place with respect to the deployment site (i.e., tissue ingrowth may have an anti-migration effect). One or more areas (such as adjacent tissue surrounding a body passage, or along the body passage through which the occlusion device is deployed) may be selected (generally limited in area, and a small proportion relative to the coated areas, such as 25% or less than the total area) to allow tissue ingrowth such as for an anti-migration effect.

The simple design of the occlusion device of the present disclosure may allow for in situ adjustments of the frame elements based on variations in anatomy and accompanying variations in the length of the body passage to ensure a secure fit or seating of the expandable portions with respect to the body passage. For instance, different sizes of collars for positioning over the intermediate region may define different lengths of the intermediate region which may affect seating of the expandable portions of the occlusion device.

In accordance with another aspect of the present disclosure, frame elements form one of the expandable portions of the occlusion device, and the other expandable portion may be formed as a flexible material substantially impermeable to the flow of materials therethrough without accompanying frame elements to support or otherwise define such expandable portion. In particular, occlusive material such as described above (used to form the occlusive material blocking flow between spaced apart frame elements) may be formed (e.g., molded, pressed, cut/stitched) into one of the portions of the occlusion device in a shape (size, thickness, etc.) and configuration sufficiently resistant to bending or flexing in response to natural forces within the body so that such portion of the occlusion device is resistant to migration with respect to the deployment site independently of (and without) frame elements therealong. On the other hand, the occlusive material and/or the size and configuration of the occlusion device portion formed from such material should be selected to be sufficiently flexible to allow a sufficiently compact configuration for deployment and/or removal of the occlusion device. In some embodiments, the impermeable material may be a semi-permeable material allowing some degree of material flow therethrough, or flow of certain materials without allow flow of other materials therethrough. In some embodiments, the material may inhibit tissue ingrowth. A removal device, such as a loop of material, may be provided along portion of such occlusion device to facilitate removal of the occlusion device if desired. It will be appreciated that the other portion of the occlusion device may be formed from frame elements as described with respect to the embodiment described above, with or without an occlusive material as described above.

Devices, systems, and methods in accordance with various principles of the present disclosure may be used with various procedures. For example, devices, systems, and methods in accordance with various principles of the present disclosure may be used with gastric procedures which involve controlling or occluding flow of gastric materials from the stomach through the pylorus, such as bariatric treatments, or treatments of related or other conditions (e.g., diabetes, or other gastrointestinal conditions). For instance, various protocols involve reducing and/or slowing the rate of passage of materials through the pylorus and/or occluding/excluding the pylorus from the stomach. Surgical procedures such as bariatric surgery (e.g., to restrict a portion of the stomach and/or to bypass portions of the intestines) may be the best or even only option for patients categorized as morbidly obese. Such procedures may have significant side effects, and often require fairly invasive surgical procedures with associated complications, tissue trauma, and/or infections, which in some instances may put the patient at risk. An occlusion device formed in accordance with various of the above-described principles or aspects addresses many if not most or all concerns by being minimally invasive, capable of being delivered and deployed and even removed (if desired or needed) in a minimally invasive manner.

In accordance with one aspect of the present disclosure, a method of treatment utilizing an occlusion device involves use of a delivery device to deliver the occlusion device to the anatomical site to be occluded (generally referenced herein as the deployment site). The delivery device may include a flexible tubular element (e.g., a catheter, sheath, shaft, endoscope, etc.) in which the occlusion device is contained in a compact delivery configuration. The method further includes deploying the occlusion device, such as by withdrawing the delivery device proximally, or by utilizing a pusher to distally move the occlusion device out of the delivery device, or a combination thereof. Moreover, because of the more compact configuration of an occlusion device formed in accordance with various principles of the present disclosure, the flexible tubular element may more readily navigate to a deployment site than may flexible tubular elements with prior, more bulky, occlusion devices. Given the low profile of the occlusion device of the present disclosure, and optionally the lack of any lumens therethrough, the delivery device may include a separate guide wire lumen, such as a lumen defined through an overtube extending along and outside the lumen through which the occlusion device is delivered.

An example of an environment in which devices, systems, and methods of the present disclosure may be used is the gastrointestinal system. However, although devices, systems, and methods are described herein with respect to a gastrointestinal system, it may be understood that embodiments of devices, systems, and methods in accordance with the present disclosure may be advantageous for use in other procedures and/or anatomical structures.

Various embodiments of occlusion devices will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/ or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

Figure 6A:
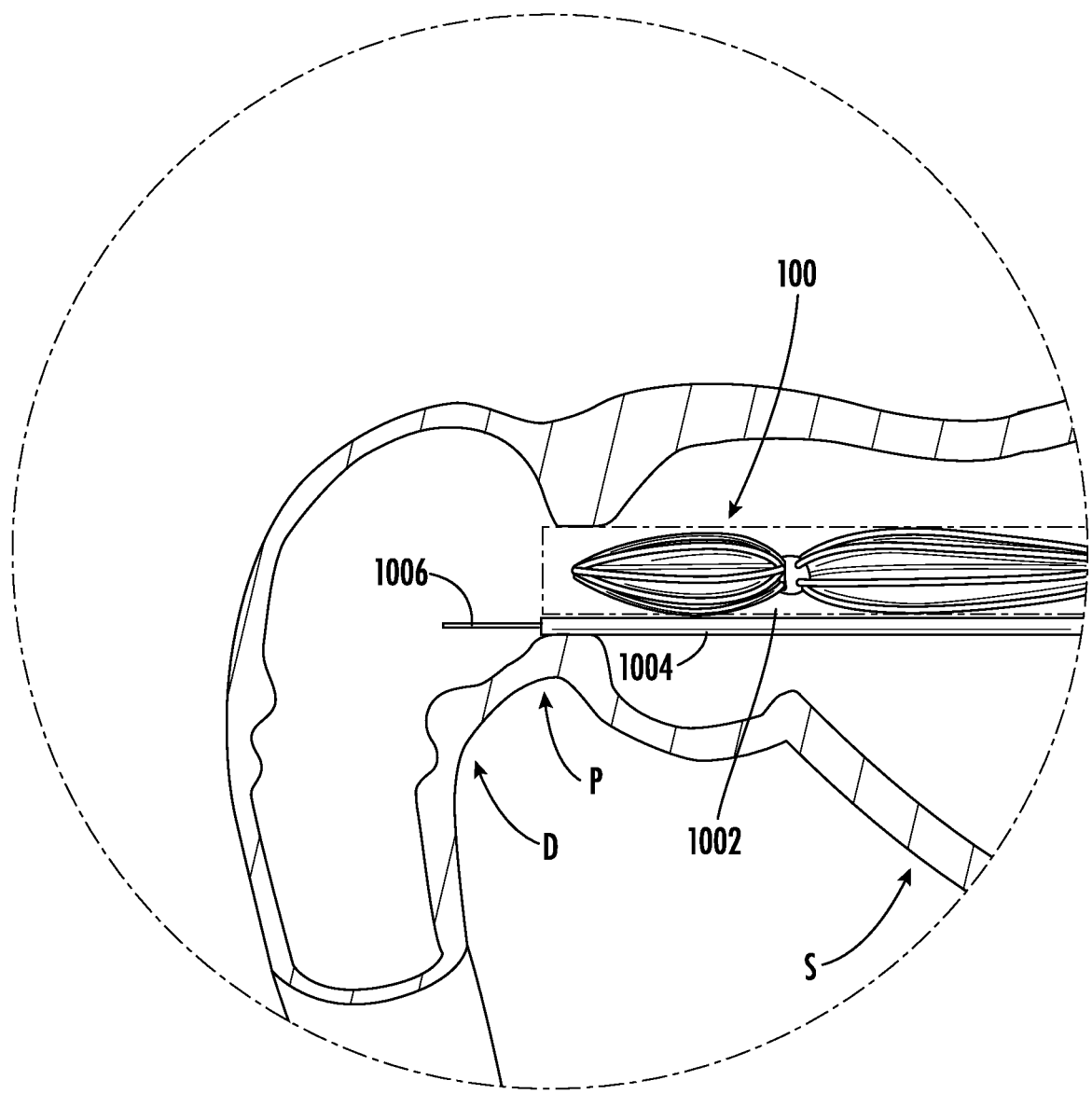
FIG. 6A illustrates a preliminary stage of delivery of an occlusion device formed in accordance with various principles of the present disclosure, such as along detail area 6A-6A of FIG. 5.

Turning now to the drawings, an example of an occlusion device 100 formed in accordance with various principles of the present disclosure is illustrated in FIG. 1 in place in a schematic representation of an example of a gastrointestinal ("GI") tract within a human body. For purposes of illustration, and without intent to limit, the occlusion device 100 shown in the drawings is described with reference to a deployment site across a pylorus P. However, it will be appreciated that an occlusion device 100 formed in accordance with various principles of the present disclosure may be positioned in or at or across other deployment sites. The illustrated example of an occlusion device 100 has a first expandable portion 110 (adjacent a first end 101 of the occlusion device 100), a second expandable portion 120 (adjacent a second end 103 of the occlusion device 100), and an intermediate region 130 therebetween. In the illustrated example of an environment, the occlusion device 100 is positioned across a pylorus P, with the first expandable portion 110 positioned within a stomach S, the second expandable portion 120 positioned within a duodenum D, and the intermediate region 130 extending between the first expandable portion 110 and the second expandable portion 120 and positioned within/extending across the pylorus P. Reference is made to "expandable" portions for the sake of convenience and without intent to limit in view of the occlusion device 100 being shiftable between a compact delivery configuration (such as illustrated in FIG. 6A) and an expanded deployed configuration such as illustrated in FIGS. 1-3 and FIG. 6C, as described in further detail below.

As may be appreciated with reference to FIG. 1, the first expandable portion 110 and the second expandable portion 120 of the illustrated embodiment have generally larger cross-sectional dimensions (e.g., width or area) than a cross-sectional dimension (e.g., a corresponding cross-sectional dimension, such as widths in generally the same direction) of the intermediate region 130. In such embodiment, the first expandable portion 110 and the second expandable portion 120 preferably are sufficiently larger than the body passage through which the intermediate region 130 extends to inhibit and preferably prevent migration of the occlusion device 100 in either direction through the body passage. In some embodiments, the first expandable portion 110 and the second expandable portion 120 may have different cross-sectional shapes or dimensions or volumes. Accordingly, the first expandable portion 110 and the second expandable portion 120 may not be symmetrical and/or may not have the same dimensions (e.g., cross-sectional or longitudinal dimensions), although other configurations (such as symmetrical configurations) are within the scope and spirit of the present disclosure. In the example of an environment illustrated in FIG. 1, the first expandable portion 110 is positioned within the stomach S and the second expandable portion 120 is positioned in the duodenum D and the intermediate region 130 is extended through the pylorus P. The first expandable portion 110 and the second expandable portion 120 preferably are large enough and provide sufficient resistance to collapsing to inhibit and preferably prevent migration of the occlusion device 100 through the pylorus P. It will be appreciated that terms such as positioned, deployed, extended, etc. (including conjugations thereof) may be used interchangeably herein without intent to limit.

Figure 2:
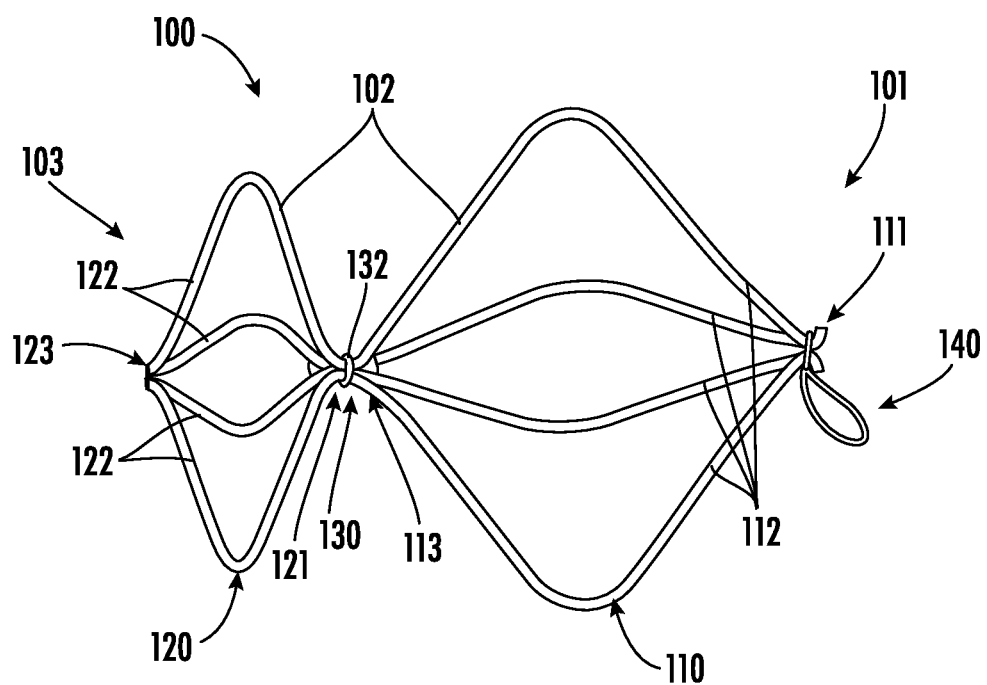
FIG. 2 illustrates an elevational view of an example of an embodiment of a structure for an occlusion device formed in accordance with various aspects of the present disclosure.
Figure 3:
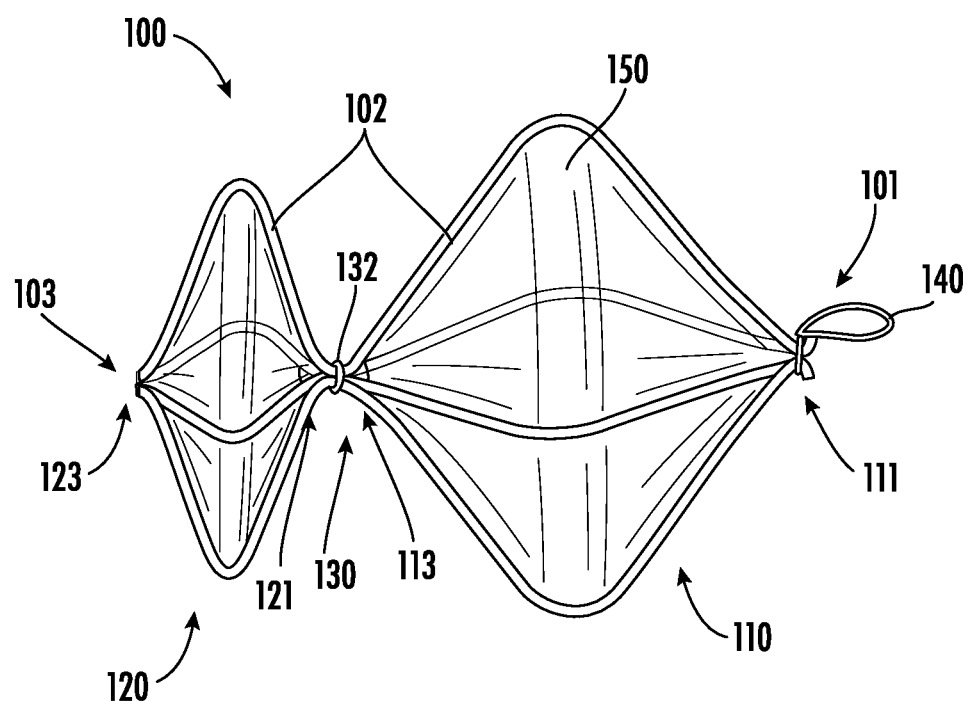
FIG. 3 illustrates an elevational view of an example of an embodiment of an occlusion device formed in accordance with various aspects of the present disclosure.

In accordance with an aspect of the present disclosure, a plurality of longitudinally extending elongated elements (e.g., strands or wires or filaments or the like) extend along at least a portion of an occlusion device 100 formed in accordance with various principles of the present disclosure such as illustrated in the embodiments of FIG. 2 and FIG. 3. The elongated elements are referenced herein for the sake of convenience and without intent to limit as frame elements 112, 122, and may be considered to define at least a portion of at least a contour of at least one of the first expandable portion 110 or the second expandable portion 120. At least one of the frame elements 112, 122, may extend continuously along (and optionally also form or define) the first expandable portion 110 and the second expandable portion 120 of the occlusion device 100. Provision of at least one such continuous frame element 112, 122, may ensure the first expandable portion 110 and the second expandable portion 120 do not separate from each other. In some embodiments, such at least one continuous frame element 112, 122 may simply extend along, but not form (e.g., not be contoured to shift with) the first expandable portion 110 and the second expandable portion 120. More than one of the frame elements 112, 122, may extend from the first end 101 to the second end 103 of the occlusion device 100, along both the first expandable portion 110 and the second expandable portion 120. Alternatively or additionally, separate frame elements 112, 122 may be used for the first expandable portion 110 and the second expandable portion 120 of the occlusion device 100. At least some of the frame elements 112 of the first expandable portion 110 may be coupled to frame elements 122 of the second expandable portion 120. Additionally or alternatively, the first expandable portion 110 and the second expandable portion 120 may be otherwise coupled together (e.g., to a separate section along the intermediate region 130) to form, together, the occlusion device 100. In some embodiments, at least some of the frame elements 112 extend from a first end 111 of the first expandable portion 110 (adjacent the first end 101 of the occlusion device 100) to a second end 113 of the first expandable portion 110 adjacent the intermediate region 130, ending at the intermediate region 130. Similarly, in some embodiments, at least some of the frame elements 122 extend from (and begin at) a first end 121 of the second expandable portion 120 (adjacent the intermediate region 130) to a second end 123 of the second first expandable portion 120 (adjacent the second end 103 of the occlusion device 100). The ends of the frame elements 112, 122 along the intermediate region 130 may be coupled together. The intermediate region 130 may include a sleeve 132 or other element covering the coupled free ends of the frame elements 112, 122 of the first expandable portion 110 and the second expandable portion 120. The sleeve may also differentiate the frame elements 112, 122 (e.g., if extending continuously across the occlusion device 100) to distinguish (e.g., the contours of) the first expandable portion 110 from the second expandable portion 120. The free ends of the frame elements 112 along the first end 101 of the first expandable portion 110, may be coupled together to form the first end 101 of the occlusion device 100. Similarly, the free ends of the frame elements 122 along the second end 103 of the second expandable portion 120 may be coupled together to form the second end 103 of the occlusion device 100. In some embodiments, the free ends of the frame elements 112, 122 may be crimped and coupled together along respective ends 111, 123 of the occlusion device 100. In the example of an embodiment illustrated in FIG. 2, a removal device 140 is provided at the first end 101 of the occlusion device 100 and may be a loop (e.g., of wire, suture material, etc.) extending around or coupled to (e.g., welded, fused, glued, etc.) the free ends of the frame elements 112 forming the first expandable portion 110 and coupled together along the first end 101 of the occlusion device 100. The removal device 140 may be used to grasp and remove the occlusion device 100 if desired, as discussed in further detail below.

The extent or length of the frame elements 112 along the first expandable portion 110 of the occlusion device 100 may be greater than the length of the frame elements 122 along the second expandable portion 120 of the occlusion device 100. Such formation allows the first expandable portion 110 to have a sufficiently large enough cross-sectional dimension when expanded in the delivery configuration to remain seated in a stomach S (or other body cavity or anatomical structure at an end of a body passage through which the occlusion device 100 is positioned) and not migrate through the pylorus P. Alternatively or additionally, the diameter of the frame elements 112 in the first expandable portion 110 of the occlusion device 100 may be different from (such as larger than) the diameter of the frame elements 122 in the second expandable portion 120 of the occlusion device 100. For instance a continuous frame element 112, 122 extending through both the first expandable portion 110 and the second expandable portion 120 may have different ground diameters along its length (for positioning in different portions 110, 120 of the occlusion device 100). Alternatively or additionally, different frame elements 112, 122, with different properties (e.g., size, diameter, resiliency, etc.) may be used in each expandable portion 110, 120, respectively, of the occlusion device 100.

The frame elements 112, 122 of an occlusion device 100 formed in accordance with various principles of the present disclosure may be formed of a biocompatible shape-memory or heat formable material. In accordance with various principles of the present disclosure, the occlusion device 100 is configured to be shifted between a compact configuration facilitating transluminal or transcatheter or endoscopic delivery, and an expanded deployed configuration, such as illustrated in FIGS. 1-3 and described above. As such, in accordance with an aspect of the present disclosure, the frame elements 112, 122 are configured to shift between an elongated, substantially straight configuration (when the occlusion device 100 is in a compact delivery configuration) to a bent or curved or nonlinear or otherwise not straight configuration to form at least a portion of the contour of the first expandable portion 110 and the second expandable portion 120 in their expanded configurations. More particularly, when the occlusion device 100 is being delivered, the dimensions of the occlusion device 100 must be reduced to fit within a delivery device (e.g., within a lumen of a flexible tubular element of a delivery device), and the frame elements 112, 122 are held or maintained in an elongated, substantially straightened configuration. Once the occlusion device 100 is deployed and moved out of the delivery device, the frame elements 112, 122 are permitted to move to a pre-set or pre-formed configuration to shift the occlusion device 100 into the expanded configuration with the first expandable portion 110 and the second expandable portion 120 in their expanded configurations.

In accordance with some aspects of the present disclosure, when the occlusion device 100 is in the expanded configuration, such as in the examples illustrated in FIGS. 1-3, one or more of the frame elements 112, 122 are configured to form at least one of the first expandable portion 110 and the second expandable portion 120 such that at least one of the first expandable portion 110 and the second expandable portion 120 seats securely with respect to a body passage to be occluded by the occlusion device 100 to occlude flow of materials therethrough. For instance, one or more of the frame elements 112, 122 may be shaped or configured to follow the natural contour of the anatomical structure along which the associated expandable portion 110, 120 is to be deployed. Thus, once the occlusion device 100 is deployed and in the expanded configuration, the one or more frame elements 112, 122 may return to their pre-set/preconfigured shape following the contour of the deployment site in a manner to achieve the desired occlusion. For instance, with reference to the example of an environment illustrated in FIG. 1, the frame elements 112, 122 of at least one of the first expandable portion 110 or the second expandable portion 120 may be shaped and/or configured to seat (along with the associated expandable portion 110, 120 formed from such frame element 112, 122) securely with respect to the pylorus P to occlude flow therethrough. More particularly, one or more of the frame elements 112 forming the first expandable portion 110 are contoured to follow the contour of the stomach S and/or tissue surrounding the entrance to the pylorus P (e.g., the pyloric antrum between the pylorus P and the stomach S). Likewise, one or more of the frame elements 122 forming the second expandable portion 120 are contoured to follow the contour of the duodenum D and/or tissue surrounding the pyloric canal connecting the pylorus P and the duodenum D.

Additionally or alternatively, one or more of the frame elements 112, 122 are configured to form at least one of the first expandable portion 110 and the second expandable portion 120 such that the at least one of the first expandable portion 110 and the second expandable portion 120 holds the other of the at least one of the first expandable portion 110 and the second expandable portion 120 in place with respect to a body passage. As such, the expandable portion 110, 120 held in place with respect to a body passage effectively occludes flow of materials through the body passage. For instance, with reference to the example of an environment illustrated in FIG. 1, one or more of the frame elements 122 of at least the second expandable portion 120 may be shaped and/or configured to hold the first expandable portion 110 securely against the entrance to the pylorus P to occlude flow of materials through the pylorus P. Similarly, one or more of the frame elements 112 of the first expandable portion 110 may be shaped and/or configured to hold the second expandable portion 120 securely against the distal end of the pylorus P to occlude flow of materials from the pylorus P and into the duodenum D.

It will be appreciated that, in accordance with various principles of the present disclosure, in order to occlude flow of materials through an expandable portion 110, 120 formed from a plurality of spaced apart elongated frame elements 112, 122 as described above, an occlusive material is provided to close or cover or fill gaps between one or more of the frame elements 112, 122. An example of an occlusive material 150 covering the first expandable portion 110 and the second expandable portion 120 of an example of an occlusion device 100 as illustrated in FIG. 2 is illustrated in FIG. 3. It will be appreciated that reference is made herein to covering (and other conjugations and grammatical forms thereof) for the sake of convenience, without intent to limit, and should be understood to include other manners and forms of providing an occlusive material 150 with respect to at least a portion of the occlusion device 100. In the illustrated example, the occlusive material 150 extends across spaces between frame elements 112, 122 to occlude flow of material therethrough. As described in greater detail above, the material and/or formation of the occlusive material 150 may be selected based on the environment in which the occlusion device 100 is deployed and to achieve the desired occlusion effect. Also as discussed in greater detail above, if the occlusive material 150 is formed from a material which inhibits tissue ingrowth, selected regions of the occlusion device 100 may be remain free of (not covered by) the occlusive material 150 to permit some tissue ingrowth with respect to the occlusion device 100 for anti-migration purposes.

Figure 4:
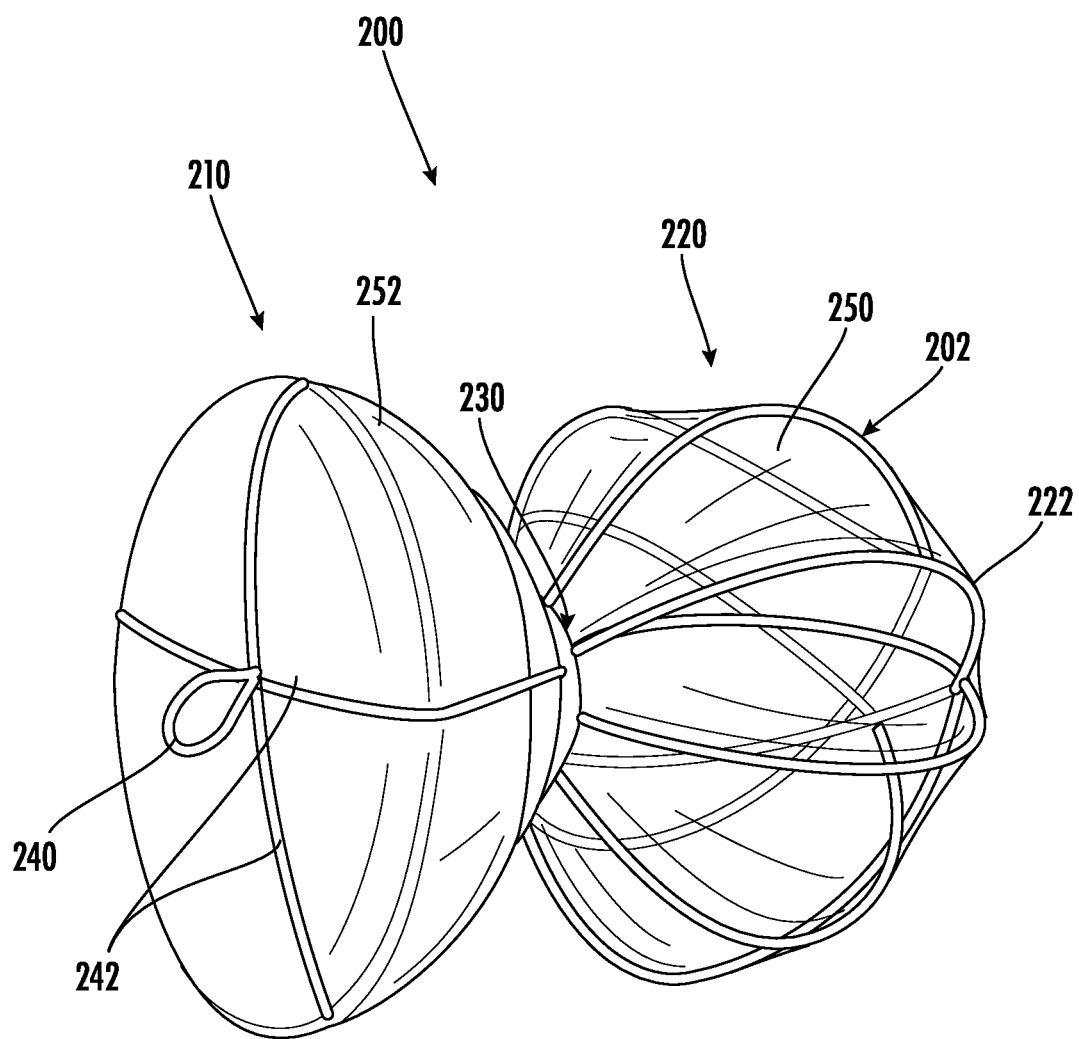
FIG. 4 illustrates an elevational view of another example of an embodiment of an occlusion device formed in accordance with various aspects of the present disclosure.

In accordance with another aspect of the present disclosure, an occlusion device 200, such as the example of an embodiment illustrated in FIG. 4, may have a first expandable portion 210 formed of a substantially continuous occlusive material 252 without the need for frame elements supporting such occlusive material 252. The occlusive material 252 may be a substantially solid component formed from a material substantially impermeable to the material to be occluded by the occlusion device 200. Such element may be molded or otherwise formed in the desired shape or configuration, such as to seat against an anatomical structure along which flow of materials is to be occluded (e.g., along an entrance to the pylorus P). The second expandable portion 220 of the example of an occlusion device 200 illustrated in FIG. 4 may be formed from frame elements 222 similar to the frame elements 122 described above. The first expandable portion 210 and the second expandable portion 220 may be coupled along the intermediate region 230 in any appropriate manner known or heretofore known (such as mechanical deformation or couplings, welding, adhesives, fusing of materials, etc.). Because frame elements may not extend along the first expandable portion 210, a removal device 240 may be coupled to or about the first expandable portion 210 in a different manner than the removal device 140 is coupled to the occlusion device 100 of the embodiment illustrated in FIG. 3. For example, the removal device 240 may include extensions 242 extending around the first expandable portion 210 to secure or couple the removal device 240 to the first expandable portion 210. It will be appreciated that elements or components of the occlusion device 200 illustrated in FIG. 4 similar to elements or components of the occlusion device 100 illustrated in FIG. 2 or FIG. 3 are generally designated with the same reference numbers increased by 100 and redundant description is omitted. For the sake of brevity, descriptions of common features are generally not repeated. The first expandable portion 210 of the occlusion device 200 illustrated in FIG. 4 is similarly collapsible into a compact configuration as is the first expandable portion 110 of the occlusion device 100 illustrated in FIG. 2 and FIG. 3 to facilitate delivery and or removal.

To deliver an occlusion device formed in accordance with principles of the present disclosure, the distal end of the flexible tubular element of the delivery device may be advanced to or distal to the deployment site with the occlusion device therein. The flexible tubular element may be withdrawn to allow the distal portion of the occlusion device to expand distal to the deployment site. Alternatively, the occlusion device may be pushed distal to the distal end of the delivery device (which may or may not be distal to the deployment site). If the deployment site is a body passage, then the distal portion of the occlusion device is positioned so that the intermediate region of the occlusion device is extended through the body passage (e.g., the occlusion device may be moved proximally so that the distal portion is seated against the outlet of the body passage and/or tissue wall surrounding the outlet of the body passage). The flexible tubular element is further withdrawn to unsheathe and allow expansion of the proximal portion of the occlusion device proximal to the deployment site (e.g., body passage). The occlusion device may be removed by holding or pulling a removal device coupled to the occlusion device to move the occlusion device into a flexible tubular element, whereupon the occlusion device is returned to a compact configuration for removal (e.g., substantially reversing the process of deploying the occlusion device). Removal of the occlusion device may be desirable if the treatment has been deemed successful and use of the occlusion device no longer indicated.

Figure 5:
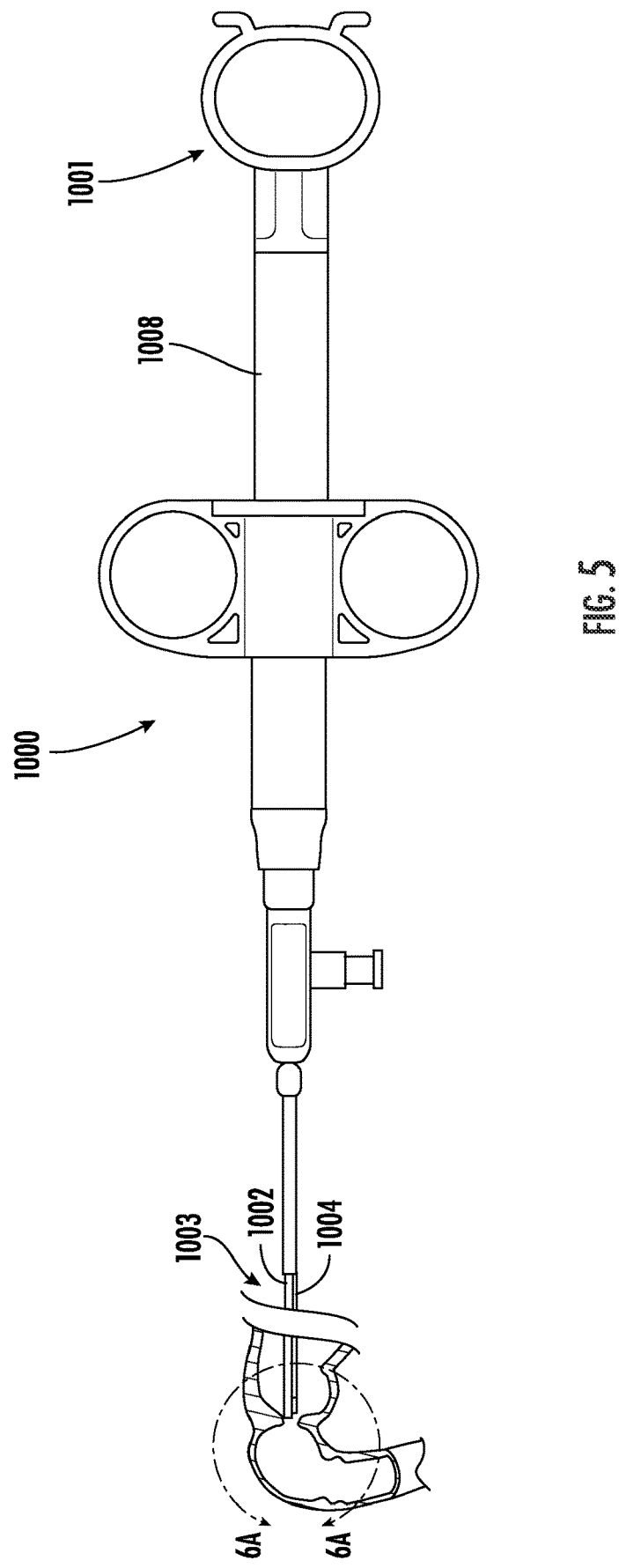
FIG. 5 illustrates an elevational view of an example of an embodiment of a delivery and deployment system which may be used with an occlusion device formed in accordance with various principles of the present disclosure.

Delivery and deployment of an occlusion device 100 formed in accordance with various principles of the present disclosure will now be described with reference to an example of a delivery device 1000 illustrated in FIG. 5. As noted above, an occlusion device 100 formed in accordance with various principles of the present disclosure is configured to be collapsed into a compact delivery configuration, such as for transcatheter or transluminal delivery. In the embodiment illustrated in FIG. 5, the delivery device 1000 includes a flexible tubular element 1002 such as a catheter, sheath, shaft, or other generally flexible elongate delivery member with a lumen therethrough as known or heretofore known in the art. The occlusion device 100 in the compact delivery configuration is capable of readily fitting within and being transported through the lumen of the flexible tubular element 1002 to the site at which the occlusion device 100 is to be deployed (i.e., to the deployment site). In view of various of the above-described aspects of an occlusion device 100 formed in accordance with principles of the present disclosure, it will be appreciated that the flexible tubular element 1002 with the occlusion device 100 therein is sufficiently flexible to be navigated through a natural body passage or lumen of a patient (e.g., without surgical intervention such as open surgery) to a delivery/deployment site. The flexible tubular element 1002 to the deployment site in any of a variety of known manners. In some embodiments, it may be desirable for a guidewire to extend alongside, rather than through, the occlusion device 100. A separate lumen, such as through an overtube 1004 alongside the flexible tubular element 1002, may be provided for guidewire 1006, as illustrated in more detail in FIG. 6A. A control handle 1008 along the proximal end 1001 of the delivery device 1000 may be used to navigate the flexible tubular element 1002 to the deployment site.

Figure 6B:
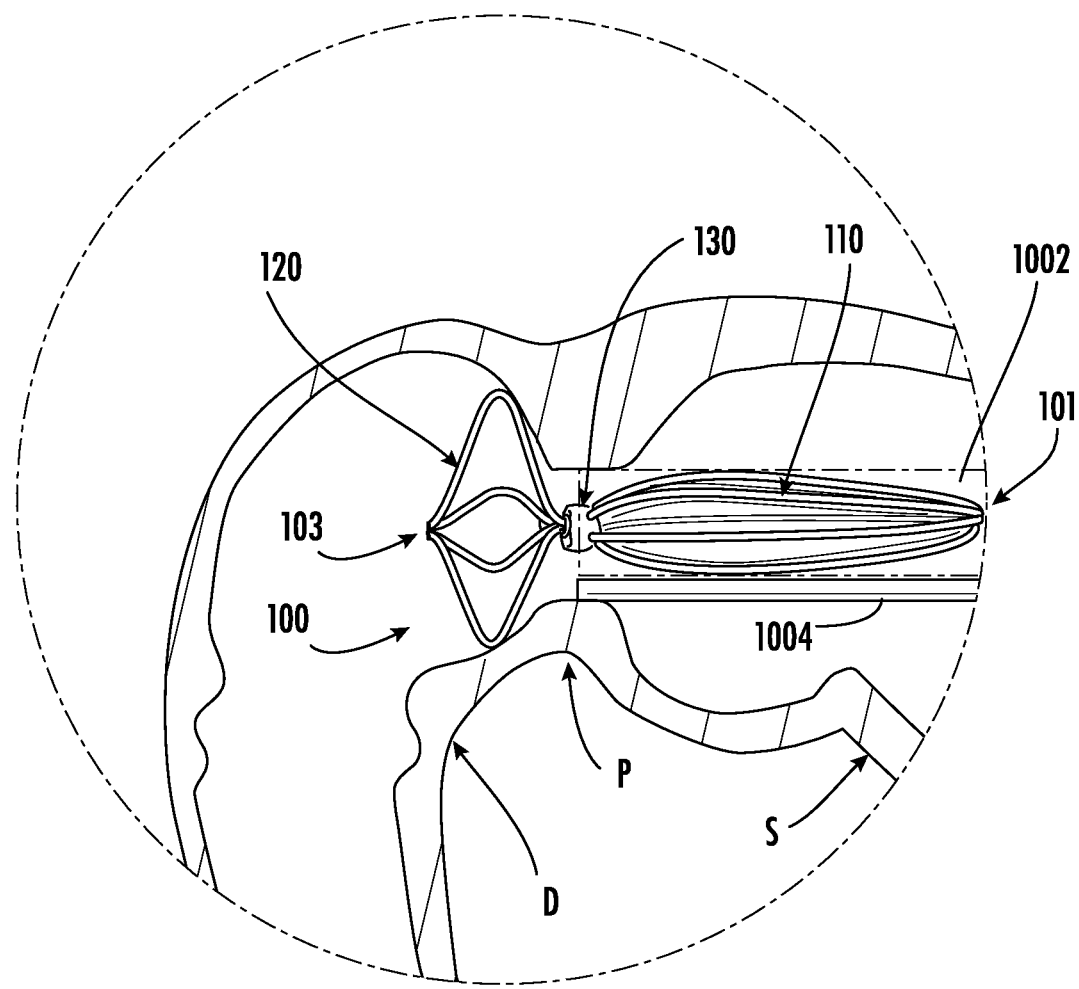
FIG. 6B illustrates deployment of a distal portion of an occlusion device formed in accordance with various principles of the present disclosure, in an environment such as illustrated in FIG. 6A.

Once the distal end 1003 of the delivery device 1000 has been advanced to or distal to the deployment site with the occlusion device therein (e.g., into the duodenum D in the illustrated example), the flexible tubular element 1002 may be withdrawn proximally to unsheathe the occlusion device 100, and/or the occlusion device 100 may be pushed out of the flexible tubular element 1002. The second expandable portion 120 of the occlusion device 100 may thus expand distal to the deployment site, as illustrated in FIG. 6B. If the deployment site is a body passage (e.g., a pylorus P, as illustrated in the example environment of FIG. 6B), then second expandable portion 120 of the occlusion device 100 is positioned so that the intermediate region 130 of the occlusion device 100 is extended through the body passage. The occlusion device 100 may be moved proximally so that the second expandable portion 120 is seated against the outlet of the body passage and/or tissue wall surrounding the outlet of the body passage.

Figure 6C:
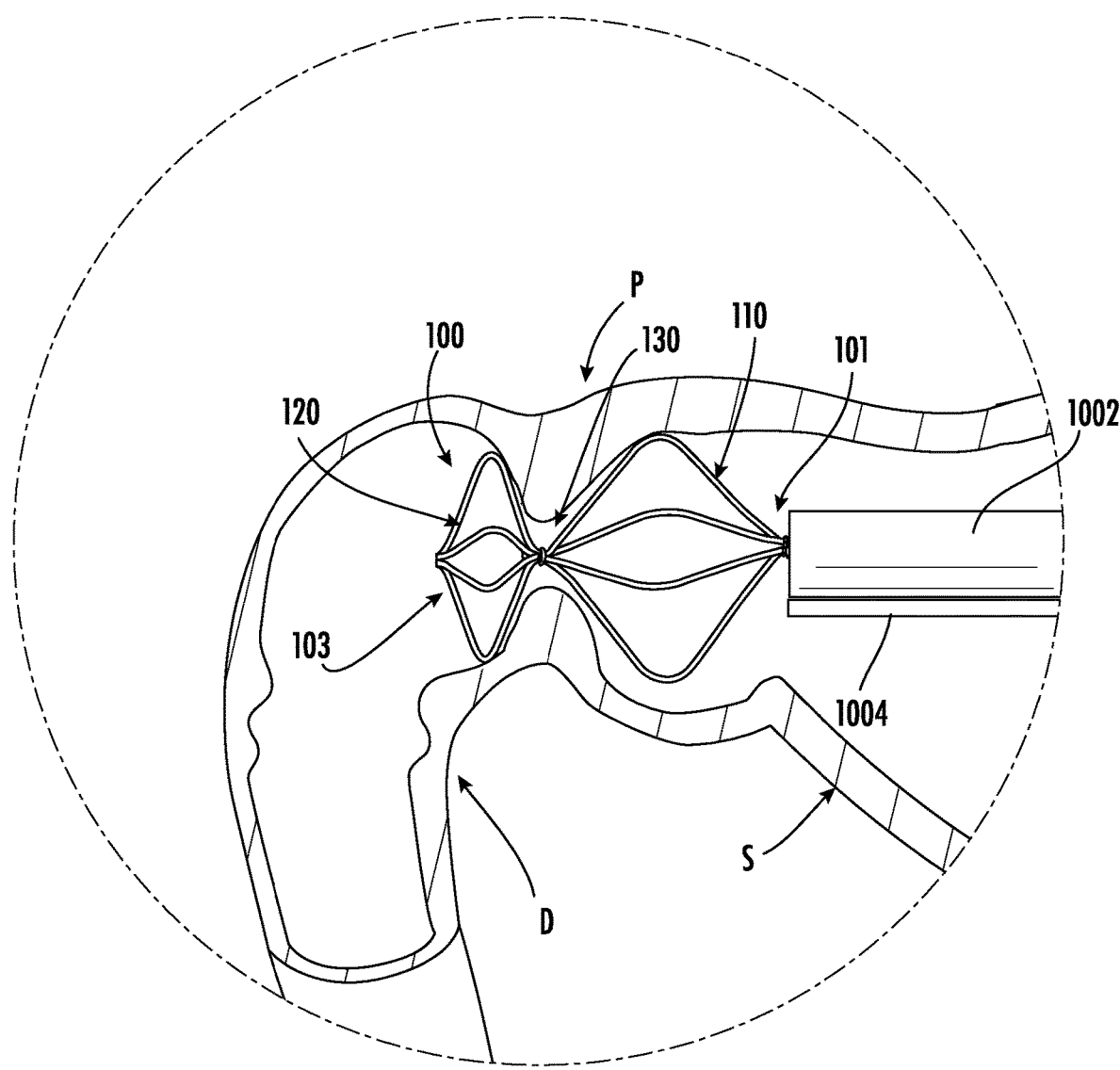
FIG. 6C illustrates deployment of a proximal portion of an occlusion device formed in accordance with various principles of the present disclosure, in an environment such as illustrated in FIG. 6A and FIG. 6B.

As illustrated in FIG. 6C, the flexible tubular element 1002 is further withdrawn proximally to unsheathe and allow expansion of the first expandable portion 110 of the occlusion device 100 proximal to the deployment site (e.g., proximal to the pylorus P and in the stomach S in the example environment illustrated in FIG. 6C). The delivery device 1000 may be removed, leaving the occlusion device 100 deployed in its expanded configuration, such as illustrated in FIG. 6C.

The occlusion device may be removed by holding or pulling a removal device coupled to the proximal end 101 of the occlusion device 100 to move the occlusion device 100 into a flexible tubular element 1002, whereupon the occlusion device 100 is returned to a compact configuration for removal (e.g., substantially reversing the process of deploying the occlusion device). Removal of the occlusion device 100 may be desirable if the treatment has been deemed successful and/or use of the occlusion device is no longer medically indicated.

It is to be understood by one of ordinary skill in the art that the above discussion is a description of illustrative examples of embodiments only, and is not intended as limiting the broader aspects of the present disclosure. All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

It will be appreciated features described with respect to one embodiment typically may be applied to another embodiment, whether or not explicitly indicated. The various features hereinafter described may be used singly or in any combination thereof. Therefore, the present invention is not limited to only the embodiments specifically described herein.

It will further be appreciated that various aspects of the above disclosure may be applied in other locations within the body to reduce flow of materials therethrough. Moreover, various features of an occlusion device formed in accordance with various principles of the present disclosure are described herein with reference to the figures and examples of environments in which an occlusion device formed in accordance with principles of the present disclosure may be used. However, it will be appreciated that the principles of the present disclosure have broader applications than the illustrated examples and the descriptions thereof.

The foregoing discussion has broad application and has been presented for purposes of illustration and description and is not intended to limit the disclosure to the form or forms disclosed herein. Various aspects of the above disclosure may be applied in other locations within the body to reduce flow of materials therethrough. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A pyloric occlusion device extending longitudinally between a first end and a second end, and configured to shift between a compact delivery configuration and an expanded deployed configuration, said occlusion device comprising:
   a first expandable portion having a first end and a second end and a pre-set shape selected to follow a contour of a portion of a stomach surrounding an entrance to a pylorus and to securely seat against the entrance to the pylorus to occlude flow of materials into the pylorus;
   a second expandable portion having a first end and a second end and a pre-set shape selected to follow a contour of a portion of a duodenum surrounding a pyloric canal connecting the pylorus and the duodenum to be able to fit within the duodenum; and
   an intermediate region between said first expandable portion and said second expandable portion and having a length selected to extend through the pylorus without causing said first expandable portion or said expandable second portion to extend into the pylorus, said intermediate region not defining a lumen therethrough;
   wherein:
   at least three elongated spaced apart frame elements form said first expandable portion and said second expandable portion, said at least three plurality of frame elements extending longitudinally when said occlusion device is in the compact delivery configuration, and bending outwardly from the first end and from the second end of each of said first expandable portion and said second expandable portion to form a radially-outwardly curved configuration extending from the first end to the second end of each of said first expandable portion and said second expandable portion while extending longitudinally along a direction parallel to a longitudinal axis of said occlusion device when said occlusion device is in the expanded deployed configuration;
   at least two of said at least three plurality of frame elements are directly coupled together along the first end of said occlusion device, and along the second end of said occlusion device, along said intermediate region; and
   an occlusive material is provided with respect to at least one of said first expandable portion or said second expandable portion to block passage of material through said at least one of said first expandable portion or said second expandable portion.

2. The pyloric occlusion device of claim 1, wherein:
   said at least three of frame elements extend longitudinally in a direction extending between said first end of said occlusion device and said second end of said occlusion device leaving spaces between adjacent frame elements; and
   the occlusive material is provided with respect to said at least three of frame elements to occlude flow of material through the spaces between adjacent frame elements.

3. The pyloric occlusion device of claim 1, wherein the occlusive material is in the form of a coating over said at least three frame elements forming an occlusive barrier through the spaces between adjacent frame elements.

4. The pyloric occlusion device of claim 1, wherein said at least three frame elements form a frame over which the occlusive material is positioned to occlude flow of material through spaces between adjacent frame elements.

5. The pyloric occlusion device of claim 1, wherein the occlusive material occludes flow of material through both said first expandable portion and said second expandable portion.

6. The pyloric occlusion device of claim 5, wherein the said occlusive material covers a portion of said at least one of said first expandable portion and said second expandable portion adjacent said intermediate region of said pyloric occlusion device.

7. The pyloric occlusion device of claim 1, wherein the occlusive material is selected to occlude flow of chyme through said at least one of said first expandable portion or said second expandable portion.

8. The pyloric occlusion device of claim 1, wherein said intermediate region is defined by said at least two frame elements.

9. The pyloric occlusion device of claim 8, wherein a collar is disposed over said intermediate region to retain said at least two frame elements together to define said intermediate region.

10. The pyloric occlusion device of claim 1, wherein said at least three frame elements are coupled together along the first end of said occlusion device, along the second end of said occlusion device, and along said intermediate region.

11. The pyloric occlusion device of claim 1, wherein said at least two frame elements are coupled together along free ends thereof.

12. The pyloric occlusion device of claim 1, further comprising a collar covering said at least two frame elements along said intermediate region of said occlusion device.

13. The pyloric occlusion device of claim 12, wherein said collar distinguishes said first expandable portion from said second expandable portion.

14. The pyloric occlusion device of claim 1, wherein continous longitudinal gaps extend between said at least three frame elements from the first end of at least one of said first expandable portion and said second expandable portion to the second end of said at least one of said first expandable portion and said second expandable portion.

15. The pyloric occlusion device of claim 1, wherein said at least three frame elements are formed from shape memory material and shift between a substantially straight configuration, when said occlusion device is in the compact delivery configuration, and a nonlinear configuration, when said occlusion device is in the expanded deployed configuration, to define a portion of said at least one of said first expandable portion and said second expandable portion.

16. A pyloric occlusion device extending longitudinally along a longitudinal axis between a first end and a second end and shaped and configured to occlude flow of material through a pylorus, said occlusion device comprising:
a first expandable portion configured to shift between a compact delivery configuration and an expanded deployed configuration;
a second expandable portion configured to shift between a compact delivery configuration and an expanded deployed configuration;
an intermediate region between said first expandable portion and said second expandable portion; and
at least three elongated frame elements extending longitudinally along a direction parallel to the longitudinal axis of said occlusion device between the first end of said occlusion device and the second end of said occlusion device, and defining at least a portion of said first expandable portion and said second expandable portion;
wherein:
at least two of said at least three elongated frame elements are connected end to end such that they are directly coupled together at said first end of said occlusion device, at said second end of said occlusion device, and at said intermediate region;
said at least three elongated frame elements are formed from shape memory material and shift between a delivery configuration capable of insertion through a body passage to a stomach, and an expanded deployed configuration;
said at least three elongated frame elements defining said first expandable portion have a pre-set shape selected to follow a contour of a portion of the stomach surrounding an entrance to the pylorus to be shaped to be securely seated against the entrance to the pylorus to occlude flow of materials into the pylorus;
said at least three elongated frame elements defining said second expandable portion have a pre-set shape selected to follow a contour of a portion of a duodenum surrounding a pyloric canal connecting the pylorus and the duodenum to be able to fit within the duodenum; and
said intermediate region has a length selected to extend through the pylorus without causing said first expandable portion or said second expandable portion to extend into the pylorus and does not define a lumen therethrough.

17. The pyloric occlusion device of claim 16, wherein said at least three elongated frame elements are spaced apart leaving spaces therebetween.

18. The pyloric occlusion device of claim 17, further comprising an occlusive material covering the spaces between said at least three elongated frame elements at least along said first expandable portion of said occlusion device.

19. A system for occluding flow of material through a pylorus, said system comprising:
a delivery device comprising a flexible tubular element with a delivery lumen defined therein; and
an occlusion device configured to fit within the delivery lumen of said flexible tubular element in a compact delivery configuration and to expand into an expanded deployed configuration when deployed out of said delivery device;
wherein:
said occlusion device comprises a first expandable portion adjacent a first end of said occlusion device, the first expandable portion having a first end and a second end, and a second expandable portion adjacent a second end of said occlusion device, the second expandable portion having a first end and a second end, and an intermediate region therebetween;
said first expandable portion and said second expandable portion are each formed from a plurality of elongated frame elements extending in a direction between said first end of said occlusion device and said second end of said occlusion device, and spaced apart from one another to leave spaces between adjacent longitudinally-extending spaced apart elongated frame elements;
said plurality of elongated frame elements extend in a substantially straight elongated configuration within said flexible tubular element of said delivery device when said occlusion device is in the compact delivery configuration, and shift to a radially-outwardly extending configuration to define a contour of said first expandable portion selected to follow a contour of a portion of a stomach surrounding an entrance to the pylorus and to securely seat against the entrance to the pylorus to occlude flow of materials into the pylorus, and said second expandable portion in the expanded deployed configuration of said occlusion device with said plurality of elongated frame element bending outwardly from the first end and from the second end of each of said first expandable portion and said second expandable portion to form a radially-outwardly curved configuration extending from the first end to the second end of each of said first expandable portion and said second expandable portion while extending longitudinally along a direction parallel to a longitudinal axis of said occlusion device to follow a contour of a portion of a duodenum surrounding a pyloric canal connecting the pylorus and the duodenum to be able to fit within the duodenum when said occlusion device is in the expanded deployed configuration; and
at least two of said plurality of elongated frame elements extends along said first expandable portion and said second expandable portion, and are directly coupled together along the first end of said first expandable portion, along the second end of said second expandable portion, and along said intermediate region.

20. The system of claim 19, further comprising an occlusive material provided with respect to at least one of said first expandable portion and said second expandable portion to occlude flow of material through said at least one of said first expandable portion and said second expandable portion and the pylorus, said occlusive material being collapsible to a compact delivery configuration when said occlusion device is within said flexible tubular element of said delivery device.

\* \* \* \* \*